(12) United States Patent
Jiang

(10) Patent No.: US 11,511,079 B2
(45) Date of Patent: Nov. 29, 2022

(54) APPARATUSES AND METHODS FOR MONITORING TENDONS OF STEERABLE CATHETERS

(71) Applicant: Auris Health, Inc., Redwood City, CA (US)

(72) Inventor: Allen Jiang, Fremont, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 17/071,816

(22) Filed: Oct. 15, 2020

(65) Prior Publication Data

US 2021/0023340 A1     Jan. 28, 2021

Related U.S. Application Data

(63) Continuation of application No. 16/696,906, filed on Nov. 26, 2019, now Pat. No. 10,814,101, which is a continuation of application No. 15/660,736, filed on Jul. 26, 2017, now Pat. No. 10,493,241, which is a
(Continued)

(51) Int. Cl.
| | |
|---|---|
| G01R 27/00 | (2006.01) |
| G01R 27/02 | (2006.01) |
| G01R 27/08 | (2006.01) |
| G01R 31/00 | (2006.01) |
| A61M 25/01 | (2006.01) |
| A61B 34/30 | (2016.01) |
| A61B 18/00 | (2006.01) |
| A61B 90/00 | (2016.01) |

(52) U.S. Cl.
CPC ............. *A61M 25/0147* (2013.01); *A61B 2018/00875* (2013.01); *A61B 2034/301* (2016.02); *A61B 2090/0809* (2016.02); *A61M 2205/33* (2013.01)

(58) Field of Classification Search
CPC ........ G01R 27/00; G01R 27/02; G01R 27/08; G01R 31/00; A61M 25/00; A61M 25/01; A61M 25/092; A61M 36/12; A61N 7/02; A61B 19/00; A61B 19/2203; A61B 5/0408; A61B 5/05; A61B 18/14
See application file for complete search history.

(56) References Cited

U.S. PATENT DOCUMENTS

| | | | |
|---|---|---|---|
| 3,572,325 A | 3/1971 | Bazell et al. | |
| 3,892,228 A | 7/1975 | Mitsui | |
| 3,913,565 A | 10/1975 | Kawahara | |

(Continued)

FOREIGN PATENT DOCUMENTS

| | | |
|---|---|---|
| CN | 1846181 | 10/2006 |
| CN | 1857877 | 11/2006 |

(Continued)

*Primary Examiner* — Neel D Shah
(74) *Attorney, Agent, or Firm* — Chang & Hale LLP

(57) ABSTRACT

Methods and apparatuses for detecting tension on a tendon and/or mechanical deformation (e.g., breakage) of one or more steering tendon of a steerable and flexible articulating device. Theses apparatuses may have one or more tendons that are each electrically conductive and configured to steer the apparatus when tension is applied to the proximal end of the tendon. Tension and/or breakage (or other deformation) of one or more of these tendons may be detected by monitoring the electrical resistance of the tendons.

20 Claims, 9 Drawing Sheets

Related U.S. Application Data continuation of application No. 15/084,984, filed on Mar. 30, 2016, now Pat. No. 9,744,335.

(60) Provisional application No. 62/140,344, filed on Mar. 30, 3015.

(56) References Cited

U.S. PATENT DOCUMENTS

| | | | |
|---|---|---|---|
| 4,294,234 A | 10/1981 | Matsuo | |
| 4,392,485 A | 7/1983 | Hiltebrandt | |
| 4,607,619 A | 8/1986 | Seike et al. | |
| 4,690,175 A | 9/1987 | Ouchi et al. | |
| 4,706,656 A | 11/1987 | Kubota | |
| 4,741,326 A | 5/1988 | Sidall et al. | |
| 4,745,908 A | 5/1988 | Wardle | |
| 4,748,969 A | 6/1988 | Wardle | |
| 4,750,475 A | 6/1988 | Yoshihashi | |
| 4,771,766 A | 9/1988 | Aoshiro | |
| 4,846,791 A | 7/1989 | Hattler et al. | |
| 4,869,238 A | 9/1989 | Opie et al. | |
| 4,906,496 A | 3/1990 | Hosono et al. | |
| 4,907,168 A | 3/1990 | Boggs | |
| 4,967,732 A | 11/1990 | Inoue | |
| 5,050,585 A | 9/1991 | Takahashi | |
| 5,083,549 A | 1/1992 | Cho et al. | |
| 5,106,387 A | 4/1992 | Kittrell et al. | |
| 5,108,800 A | 4/1992 | Koo | |
| 5,125,909 A | 6/1992 | Heimberger | |
| 5,168,864 A | 12/1992 | Shockey | |
| 5,217,002 A | 6/1993 | Katsurada | |
| 5,251,611 A | 10/1993 | Zehel et al. | |
| 5,257,617 A | 11/1993 | Takahashi | |
| 5,261,391 A | 11/1993 | Inoue | |
| 5,287,861 A | 2/1994 | Wilk | |
| 5,313,934 A | 5/1994 | Wiita et al. | |
| 5,386,818 A | 2/1995 | Schneebaum | |
| 5,448,988 A | 9/1995 | Watanabe | |
| 5,478,330 A | 12/1995 | Imran et al. | |
| 5,482,029 A | 1/1996 | Sekiguchi | |
| 5,489,270 A | 2/1996 | van Erp | |
| 5,507,725 A | 4/1996 | Savage et al. | |
| 5,533,985 A | 7/1996 | Wang | |
| 5,580,200 A | 12/1996 | Fullerton | |
| 5,681,296 A | 10/1997 | Ishida | |
| 5,704,534 A | 1/1998 | Huitema et al. | |
| 5,720,775 A | 2/1998 | Lamard | |
| 5,741,429 A | 4/1998 | Donadio, III | |
| 5,749,889 A | 5/1998 | Bacich et al. | |
| 5,873,817 A | 2/1999 | Kokish et al. | |
| 5,876,325 A | 3/1999 | Mizuno et al. | |
| 5,879,287 A | 3/1999 | Yoshihashi | |
| 5,882,347 A | 3/1999 | Mouris-Laan | |
| 5,888,191 A | 3/1999 | Akiba | |
| 5,910,129 A | 6/1999 | Koblish et al. | |
| 5,938,586 A | 8/1999 | Wilk | |
| 5,938,587 A | 8/1999 | Taylor et al. | |
| 6,012,494 A | 1/2000 | Balazs | |
| 6,102,926 A * | 8/2000 | Tartaglia | A61B 17/3207 |
| | | | 600/564 |
| 6,143,013 A | 11/2000 | Samson et al. | |
| 6,157,853 A | 12/2000 | Blume et al. | |
| 6,174,280 B1 | 1/2001 | Oneda | |
| 6,197,015 B1 | 3/2001 | Wilson | |
| 6,198,974 B1 | 3/2001 | Webster, Jr. | |
| 6,234,958 B1 | 5/2001 | Snoke et al. | |
| 6,315,715 B1 | 11/2001 | Taylor et al. | |
| 6,404,497 B1 | 6/2002 | Backman | |
| 6,436,107 B1 | 8/2002 | Wang et al. | |
| 6,464,632 B1 | 10/2002 | Taylor | |
| 6,485,411 B1 | 11/2002 | Konstorum | |
| 6,491,626 B1 | 12/2002 | Stone et al. | |
| 6,537,205 B1 | 3/2003 | Smith | |
| 6,554,793 B1 | 4/2003 | Pauker et al. | |
| 6,716,178 B1 | 4/2004 | Kilpatrick et al. | |
| 6,746,422 B1 | 6/2004 | Noriega | |
| 6,749,560 B1 | 6/2004 | Konstorum | |
| 6,790,173 B2 | 9/2004 | Saadat | |
| 6,827,710 B1 | 12/2004 | Mooney et al. | |
| 6,827,712 B2 | 12/2004 | Tovey et al. | |
| 6,837,846 B2 | 1/2005 | Jaffe | |
| 6,908,428 B2 | 6/2005 | Aizenfeld | |
| 6,921,362 B2 | 7/2005 | Ouchi | |
| 6,958,035 B2 | 10/2005 | Friedman et al. | |
| 7,008,401 B2 | 3/2006 | Thompson et al. | |
| 7,130,700 B2 | 10/2006 | Gardeski et al. | |
| 7,594,903 B2 | 9/2009 | Webler et al. | |
| 7,645,230 B2 | 1/2010 | Mikkaichi | |
| 7,645,231 B2 | 1/2010 | Akiba | |
| 7,771,416 B2 | 8/2010 | Spiver et al. | |
| 7,781,724 B2 | 8/2010 | Childers et al. | |
| 7,789,827 B2 | 9/2010 | Landry | |
| 7,930,065 B2 | 4/2011 | Larkin et al. | |
| 8,046,049 B2 | 10/2011 | Govari et al. | |
| 8,052,636 B2 | 11/2011 | Moll et al. | |
| 8,246,536 B2 | 8/2012 | Ochi | |
| 8,444,637 B2 | 5/2013 | Podmore et al. | |
| 8,460,236 B2 | 6/2013 | Roelle et al. | |
| 8,498,691 B2 | 7/2013 | Moll et al. | |
| 8,515,215 B2 | 8/2013 | Younge et al. | |
| 8,652,030 B2 | 2/2014 | Matsuura et al. | |
| 8,686,747 B2 * | 4/2014 | Berner | B66B 7/1223 |
| | | | 324/691 |
| 8,758,231 B2 | 6/2014 | Bunch et al. | |
| 8,827,947 B2 | 9/2014 | Bosman et al. | |
| 8,911,471 B2 | 12/2014 | Spiver et al. | |
| 9,186,046 B2 | 11/2015 | Ramamurthy et al. | |
| 9,314,953 B2 | 4/2016 | Lauer | |
| 9,427,551 B2 | 8/2016 | Leeflang et al. | |
| 9,504,604 B2 | 11/2016 | Alvarez | |
| 9,561,083 B2 | 2/2017 | Yu et al. | |
| 9,591,990 B2 | 3/2017 | Chen et al. | |
| 9,622,827 B2 | 4/2017 | Yu et al. | |
| 9,636,184 B2 | 5/2017 | Lee et al. | |
| 9,713,509 B2 | 7/2017 | Schuh et al. | |
| 9,726,476 B2 | 8/2017 | Ramamurthy et al. | |
| 9,727,963 B2 | 8/2017 | Mintz et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,788,910 B2 | 10/2017 | Schuh | |
| 9,844,353 B2 | 12/2017 | Walker et al. | |
| 9,844,412 B2 | 12/2017 | Bogusky et al. | |
| 9,867,635 B2 | 1/2018 | Alvarez et al. | |
| 9,918,659 B2 | 3/2018 | Chopra | |
| 9,918,681 B2 | 3/2018 | Wallace et al. | |
| 9,931,025 B1 | 4/2018 | Graetzel et al. | |
| 9,949,749 B2 | 4/2018 | Noonan et al. | |
| 9,955,986 B2 | 5/2018 | Shah | |
| 9,962,228 B2 | 5/2018 | Schuh et al. | |
| 9,980,785 B2 | 5/2018 | Schuh | |
| 9,993,313 B2 | 6/2018 | Schuh et al. | |
| 10,016,900 B1 | 7/2018 | Meyer et al. | |
| 10,022,192 B1 | 7/2018 | Ummalaneni | |
| 10,080,576 B2 | 9/2018 | Romo et al. | |
| 10,130,427 B2 | 11/2018 | Tanner et al. | |
| 10,136,959 B2 | 11/2018 | Mintz et al. | |
| 10,145,747 B1 | 12/2018 | Lin et al. | |
| 10,149,720 B2 | 12/2018 | Romo | |
| 10,159,532 B1 | 12/2018 | Ummalaneni et al. | |
| 10,159,533 B2 | 12/2018 | Moll et al. | |
| 10,169,875 B2 | 1/2019 | Mintz et al. | |
| 10,219,874 B2 | 3/2019 | Yu et al. | |
| 10,231,793 B2 | 3/2019 | Romo | |
| 10,231,867 B2 | 3/2019 | Alvarez et al. | |
| 10,244,926 B2 | 4/2019 | Noonan et al. | |
| 10,285,574 B2 | 5/2019 | Landey et al. | |
| 10,299,870 B2 | 5/2019 | Connolly et al. | |
| 10,314,463 B2 | 6/2019 | Agrawal et al. | |
| 10,363,103 B2 | 7/2019 | Alvarez et al. | |
| 10,376,672 B2 | 8/2019 | Yu | |
| 10,383,765 B2 | 8/2019 | Alvarez et al. | |
| 10,398,518 B2 | 9/2019 | Yu et al. | |

(56) References Cited

U.S. PATENT DOCUMENTS

| | | |
|---|---|---|
| 10,405,908 B2 | 9/2019 | Redmond et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,463,439 B2 | 11/2019 | Joseph et al. |
| 10,464,209 B2 | 11/2019 | Ho et al. |
| 10,470,830 B2 | 11/2019 | Hill |
| 10,482,599 B2 | 11/2019 | Mintz et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,539,478 B2 | 1/2020 | Lin |
| 10,543,048 B2 | 1/2020 | Noonan et al. |
| 10,555,778 B2 | 2/2020 | Ummalaneni et al. |
| 10,555,780 B2 | 2/2020 | Tanner et al. |
| 10,631,949 B2 | 4/2020 | Schuh et al. |
| 10,639,108 B2 | 5/2020 | Romo et al. |
| 10,639,109 B2 | 5/2020 | Bovay et al. |
| 10,639,114 B2 | 5/2020 | Schuh |
| 10,667,720 B2 | 6/2020 | Wong et al. |
| 10,667,871 B2 | 6/2020 | Romo et al. |
| 10,667,875 B2 | 6/2020 | DeFonzo |
| 10,682,189 B2 | 6/2020 | Schuh et al. |
| 10,702,348 B2 | 7/2020 | Moll et al. |
| 10,716,461 B2 | 7/2020 | Jenkins |
| 10,743,751 B2 | 8/2020 | Landey et al. |
| 10,744,035 B2 | 8/2020 | Alvarez et al. |
| 10,751,140 B2 | 8/2020 | Wallace et al. |
| 10,765,303 B2 | 9/2020 | Graetzel et al. |
| 10,765,487 B2 | 9/2020 | Ho |
| 10,779,898 B2 | 9/2020 | Hill |
| 10,786,329 B2 | 9/2020 | Schuh et al. |
| 10,786,432 B2 | 10/2020 | Mintz et al. |
| 10,792,464 B2 | 10/2020 | Romo et al. |
| 10,792,466 B2 | 10/2020 | Landey et al. |
| 10,813,539 B2 | 10/2020 | Graetzel et al. |
| 10,814,101 B2 | 10/2020 | Jiang |
| 10,820,947 B2 | 11/2020 | Julian |
| 10,827,913 B2 | 11/2020 | Ummalaneni et al. |
| 10,828,118 B2 | 11/2020 | Schuh et al. |
| 2001/0004676 A1 | 6/2001 | Ouchi |
| 2003/0036748 A1 | 2/2003 | Cooper et al. |
| 2003/0130564 A1 | 7/2003 | Martone et al. |
| 2003/0158545 A1 | 8/2003 | Hovda et al. |
| 2003/0163199 A1 | 8/2003 | Chu et al. |
| 2003/0195664 A1 | 10/2003 | Nowlin et al. |
| 2004/0015122 A1 | 1/2004 | Zhang et al. |
| 2004/0054322 A1 | 3/2004 | Vargas |
| 2004/0072066 A1 | 4/2004 | Cho et al. |
| 2004/0138525 A1 | 7/2004 | Saadat et al. |
| 2004/0193013 A1 | 9/2004 | Isakawa et al. |
| 2004/0249246 A1 | 12/2004 | Campos |
| 2005/0004515 A1 | 1/2005 | Hart et al. |
| 2005/0125005 A1 | 6/2005 | Fujikura |
| 2005/0131279 A1 | 6/2005 | Boulais et al. |
| 2005/0154262 A1 | 7/2005 | Banik et al. |
| 2005/0159646 A1 | 7/2005 | Nordstrom et al. |
| 2005/0165366 A1 | 7/2005 | Brustad |
| 2005/0222581 A1 | 10/2005 | Fischer et al. |
| 2005/0234293 A1 | 10/2005 | Yamamoto |
| 2005/0256452 A1 | 11/2005 | DeMarchi |
| 2005/0272975 A1 | 12/2005 | McWeeney et al. |
| 2005/0273085 A1 | 12/2005 | Hinman et al. |
| 2005/0288549 A1 | 12/2005 | Mathis |
| 2006/0041188 A1 | 2/2006 | Dirusso et al. |
| 2006/0111692 A1 | 5/2006 | Hlavka et al. |
| 2006/0241368 A1 | 10/2006 | Fichtinger et al. |
| 2006/0264708 A1 | 11/2006 | Horne |
| 2006/0276827 A1 | 12/2006 | Mitelberg et al. |
| 2007/0060879 A1 | 3/2007 | Weitzner et al. |
| 2007/0112355 A1 | 5/2007 | Salahieh |
| 2007/0135733 A1 | 6/2007 | Soukup et al. |
| 2007/0135763 A1 | 6/2007 | Musbach et al. |
| 2007/0135803 A1 | 6/2007 | Belson |
| 2007/0156019 A1 | 7/2007 | Larkin et al. |
| 2007/0270645 A1 | 11/2007 | Ikeda |
| 2007/0270679 A1 | 11/2007 | Nguyen et al. |
| 2007/0282167 A1 | 12/2007 | Barenboym et al. |
| 2007/0287886 A1 | 12/2007 | Saadat |
| 2008/0039255 A1 | 2/2008 | Jinno et al. |
| 2008/0051629 A1 | 2/2008 | Sugiyama et al. |
| 2008/0065103 A1 | 3/2008 | Cooper et al. |
| 2008/0097293 A1 | 4/2008 | Chin et al. |
| 2008/0108869 A1 | 5/2008 | Sanders et al. |
| 2008/0139887 A1 | 6/2008 | Fitpatrick |
| 2008/0146874 A1 | 6/2008 | Miller |
| 2008/0147089 A1 | 6/2008 | Loh |
| 2008/0177285 A1 | 7/2008 | Brock et al. |
| 2008/0208001 A1 | 8/2008 | Hadani |
| 2008/0212082 A1 | 9/2008 | Froggatt et al. |
| 2008/0218770 A1 | 9/2008 | Moll et al. |
| 2008/0255470 A1* | 10/2008 | Hauck ............... A61B 5/6852 604/523 |
| 2009/0099420 A1 | 4/2009 | Woodley et al. |
| 2009/0163851 A1 | 6/2009 | Holloway |
| 2009/0247880 A1 | 10/2009 | Naruse et al. |
| 2009/0254083 A1 | 10/2009 | Wallace et al. |
| 2009/0262109 A1 | 10/2009 | Markowitz et al. |
| 2009/0299344 A1 | 12/2009 | Lee et al. |
| 2009/0306587 A1 | 12/2009 | Milijasevic et al. |
| 2010/0030023 A1 | 2/2010 | Yoshie |
| 2010/0073150 A1 | 3/2010 | Olson et al. |
| 2010/0114115 A1 | 5/2010 | Schlesinger et al. |
| 2010/0130823 A1 | 5/2010 | Ando |
| 2010/0168918 A1 | 7/2010 | Zhao |
| 2010/0217184 A1 | 8/2010 | Koblish et al. |
| 2010/0249497 A1 | 9/2010 | Peine et al. |
| 2010/0249506 A1 | 9/2010 | Prisco et al. |
| 2011/0009863 A1 | 1/2011 | Stanislaw |
| 2011/0046441 A1 | 2/2011 | Wiltshire et al. |
| 2011/0077681 A1 | 3/2011 | Nagano |
| 2011/0098533 A1 | 4/2011 | Onoda |
| 2011/0130718 A1 | 6/2011 | Kidd et al. |
| 2011/0148442 A1 | 6/2011 | Berner |
| 2011/0152880 A1 | 6/2011 | Alvarez et al. |
| 2011/0245844 A1 | 10/2011 | Jinno et al. |
| 2011/0261183 A1 | 10/2011 | Ma et al. |
| 2011/0306836 A1 | 12/2011 | Ohline et al. |
| 2012/0071894 A1 | 3/2012 | Tanner et al. |
| 2012/0071895 A1 | 3/2012 | Stahler et al. |
| 2012/0123327 A1 | 5/2012 | Miller |
| 2012/0136419 A1 | 5/2012 | Zarembo et al. |
| 2012/0143226 A1 | 6/2012 | Belson et al. |
| 2012/0190976 A1 | 7/2012 | Kleinstreuer |
| 2012/0191107 A1 | 7/2012 | Tanner et al. |
| 2012/0239012 A1 | 9/2012 | Laurent et al. |
| 2012/0259244 A1 | 10/2012 | Roberts et al. |
| 2012/0283747 A1 | 11/2012 | Popovic |
| 2012/0289777 A1 | 11/2012 | Chopra |
| 2013/0018400 A1 | 1/2013 | Milton et al. |
| 2013/0030519 A1 | 1/2013 | Tran et al. |
| 2013/0035537 A1 | 2/2013 | Wallace et al. |
| 2013/0090552 A1 | 4/2013 | Ramamurthy et al. |
| 2013/0109957 A1 | 5/2013 | Hooft et al. |
| 2013/0144116 A1 | 6/2013 | Cooper et al. |
| 2013/0165854 A1 | 6/2013 | Sandhu et al. |
| 2013/0165908 A1 | 6/2013 | Purdy et al. |
| 2013/0197556 A1 | 8/2013 | Shelton et al. |
| 2013/0204124 A1 | 8/2013 | Duindam |
| 2013/0226151 A1 | 8/2013 | Suehara |
| 2013/0303892 A1 | 11/2013 | Zhao |
| 2013/0304091 A1 | 11/2013 | Straehnz |
| 2013/0317276 A1 | 11/2013 | D'Andrea |
| 2013/0317519 A1 | 11/2013 | Romo et al. |
| 2013/0345519 A1 | 12/2013 | Piskun et al. |
| 2014/0012288 A1 | 1/2014 | Darisse |
| 2014/0046313 A1 | 2/2014 | Pederson et al. |
| 2014/0142591 A1 | 5/2014 | Alvarez et al. |
| 2014/0200402 A1 | 7/2014 | Snoke et al. |
| 2014/0235943 A1 | 8/2014 | Paris |
| 2014/0251042 A1 | 9/2014 | Asselin et al. |

(56) References Cited

U.S. PATENT DOCUMENTS

| | | |
|---|---|---|
| 2014/0276594 A1 | 9/2014 | Tanner et al. |
| 2014/0316397 A1 | 10/2014 | Brown |
| 2014/0343416 A1 | 11/2014 | Panescu |
| 2014/0357984 A1 | 12/2014 | Wallace et al. |
| 2015/0031950 A1 | 1/2015 | Drontle et al. |
| 2015/0032151 A1 | 1/2015 | Ishida et al. |
| 2015/0255782 A1 | 9/2015 | Kim et al. |
| 2016/0000414 A1 | 1/2016 | Brown |
| 2016/0007881 A1 | 1/2016 | Wong et al. |
| 2016/0067450 A1* | 3/2016 | Kowshik ............... A61B 34/71 604/95.04 |
| 2016/0183841 A1 | 6/2016 | Duindam et al. |
| 2016/0227982 A1 | 8/2016 | Takahashi |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0346049 A1 | 12/2016 | Allen et al. |
| 2016/0372743 A1 | 12/2016 | Cho et al. |
| 2017/0007337 A1 | 1/2017 | Dan |
| 2017/0197060 A1* | 7/2017 | Houck .................. A61B 5/287 |
| 2017/0202627 A1 | 7/2017 | Sramek et al. |
| 2017/0209073 A1 | 7/2017 | Sramek et al. |
| 2017/0281218 A1* | 10/2017 | Timm ............... A61B 17/2909 |
| 2017/0290631 A1 | 10/2017 | Lee et al. |
| 2018/0025666 A1 | 1/2018 | Ho et al. |
| 2018/0221038 A1 | 8/2018 | Noonan et al. |
| 2018/0221039 A1 | 8/2018 | Shah |
| 2018/0279852 A1 | 10/2018 | Rafii-Tari et al. |
| 2018/0289431 A1 | 10/2018 | Draper et al. |
| 2018/0325499 A1 | 11/2018 | Landey et al. |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0110839 A1 | 4/2019 | Rafii-Tari et al. |
| 2019/0151148 A1 | 4/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298460 A1 | 10/2019 | Al-Jadda |
| 2019/0298465 A1 | 10/2019 | Chin |
| 2019/0307987 A1 | 10/2019 | Yu |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0365491 A1 | 12/2019 | Yu |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0038123 A1 | 2/2020 | Graetzel |
| 2020/0038128 A1 | 2/2020 | Joseph |
| 2020/0039086 A1 | 2/2020 | Meyer |
| 2020/0046434 A1 | 2/2020 | Graetzel |
| 2020/0046942 A1 | 2/2020 | Alvarez |
| 2020/0060516 A1 | 2/2020 | Baez |
| 2020/0085516 A1 | 3/2020 | DeFonzo |
| 2020/0093549 A1 | 3/2020 | Chin |
| 2020/0093554 A1 | 3/2020 | Schuh |
| 2020/0100855 A1 | 4/2020 | Leparmentier |
| 2020/0107894 A1 | 4/2020 | Wallace |
| 2020/0121502 A1 | 4/2020 | Kintz |
| 2020/0138334 A1* | 5/2020 | Hill .................. A61B 5/6852 |
| 2020/0146769 A1 | 5/2020 | Eyre |
| 2020/0170720 A1 | 6/2020 | Ummalaneni |
| 2020/0171660 A1 | 6/2020 | Ho |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0305922 A1 | 10/2020 | Schuh |
| 2020/0305983 A1 | 10/2020 | Yampolsky |
| 2020/0305989 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2020/0337593 A1 | 10/2020 | Wong |
| 2020/0345216 A1 | 11/2020 | Jenkins |
| 2020/0352420 A1 | 11/2020 | Graetzel |

FOREIGN PATENT DOCUMENTS

| | | |
|---|---|---|
| CN | 102316817 | 1/2012 |
| CN | 102458295 | 5/2012 |
| CN | 102665590 | 9/2012 |
| CN | 102711586 | 10/2012 |
| CN | 102973317 | 3/2013 |
| CN | 103767659 | 5/2014 |
| CN | 103930063 | 7/2014 |
| EP | 0 543 539 | 5/1993 |
| EP | 0 776 739 | 6/1997 |
| EP | 1 442 720 | 8/2004 |
| EP | 0 904 796 | 11/2004 |
| JP | 2006-525087 | 11/2006 |
| JP | 2007-511247 | 5/2007 |
| JP | 2010-046384 | 3/2010 |
| JP | 2011-015992 | 1/2011 |
| JP | 2012-105793 | 6/2012 |
| WO | WO 94/14494 | 7/1994 |
| WO | WO 00/67640 | 11/2000 |
| WO | WO 02/74178 | 9/2002 |
| WO | WO 04/039273 | 5/2004 |
| WO | WO 04/105849 | 12/2004 |
| WO | WO 05/032637 | 4/2005 |
| WO | WO 05/081202 | 9/2005 |
| WO | WO 09/097461 | 6/2007 |
| WO | WO 07/146987 | 12/2007 |
| WO | WO 08/097540 | 8/2008 |
| WO | WO 09/092059 | 7/2009 |
| WO | WO 10/081187 | 7/2010 |
| WO | WO 11/005335 | 1/2011 |
| WO | WO 13/107468 | 7/2013 |
| WO | WO 15/093602 | 12/2013 |
| WO | WO 16/003052 | 1/2016 |

* cited by examiner

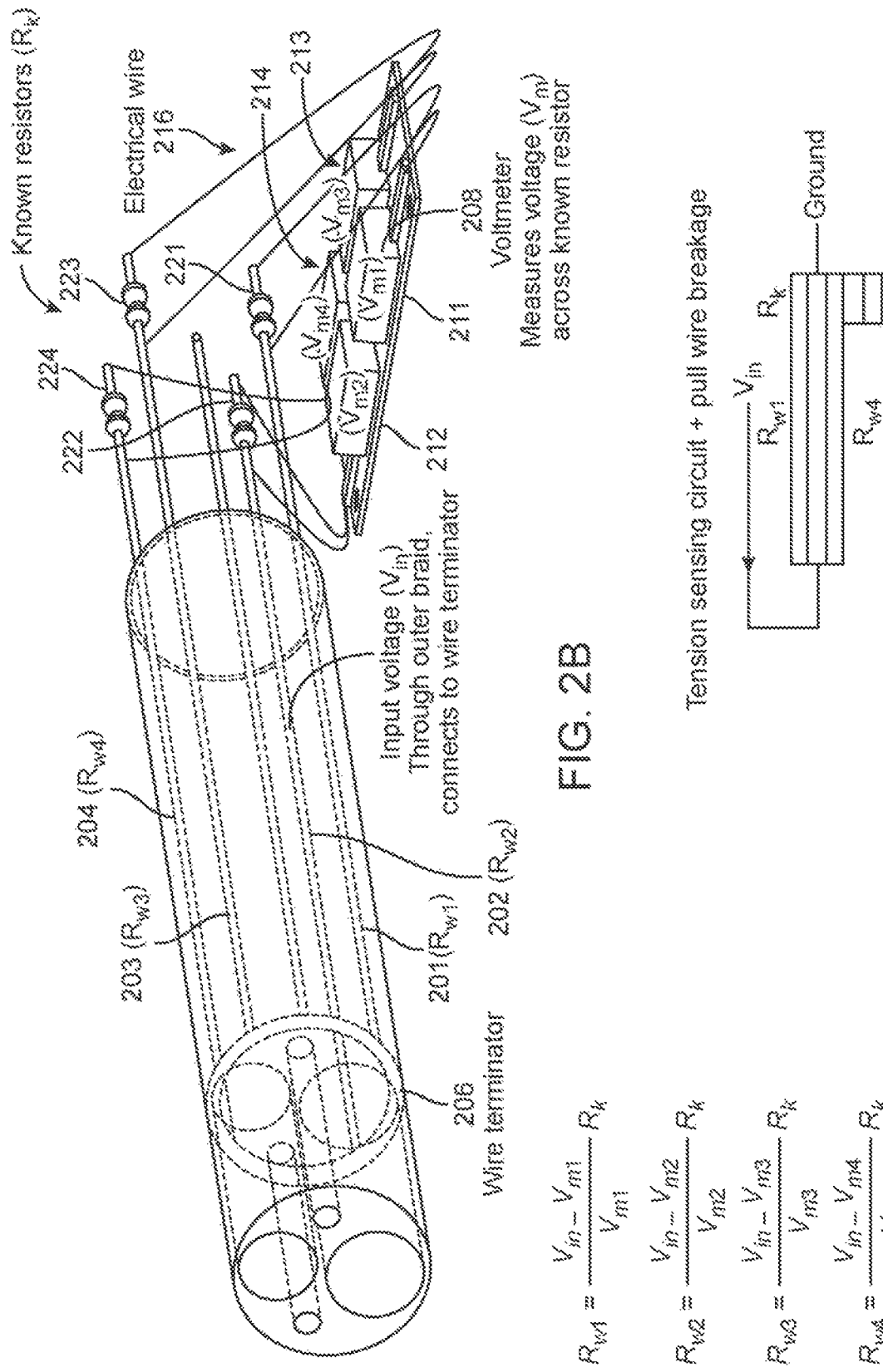

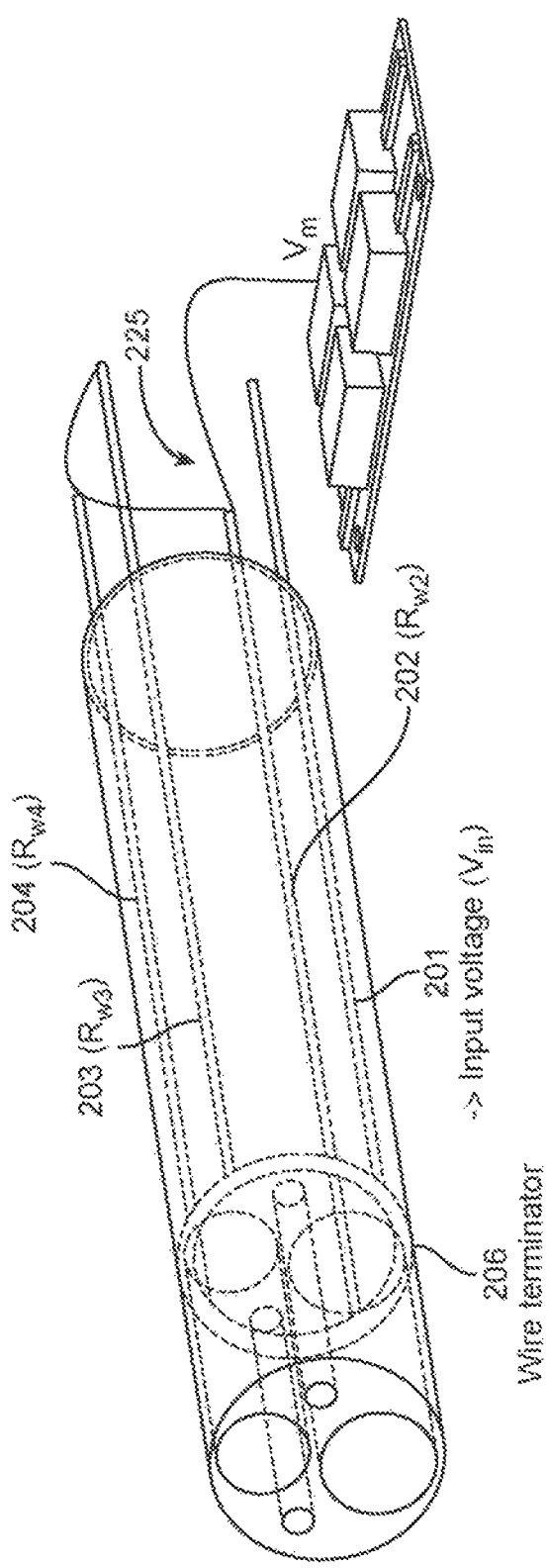
FIG. 2C
Pull wire 1 breakage
$V_m = 0$
Pull wire 2, 3, or 4 breakage
$V_m = \dfrac{V_{in}}{\left(\dfrac{R_w}{3R_k} + 1\right)} \longrightarrow V_m = \dfrac{V_{in}}{\left(\dfrac{R_w}{2R_k} + 1\right)}$
FIG. 2C1
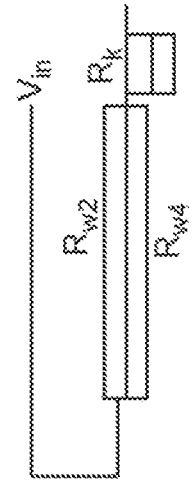
FIG. 2C2
$\dfrac{1}{R_w} = \dfrac{1}{R_{w2}} + \dfrac{1}{R_{w3}} + \dfrac{1}{R_{w4}}$

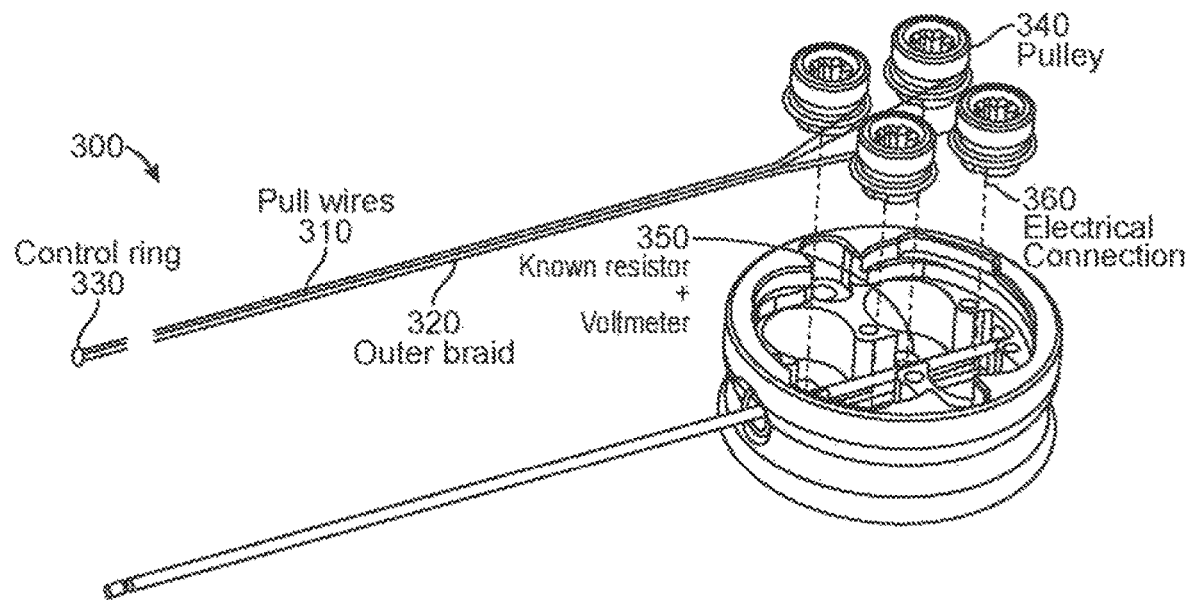
FIG. 3A
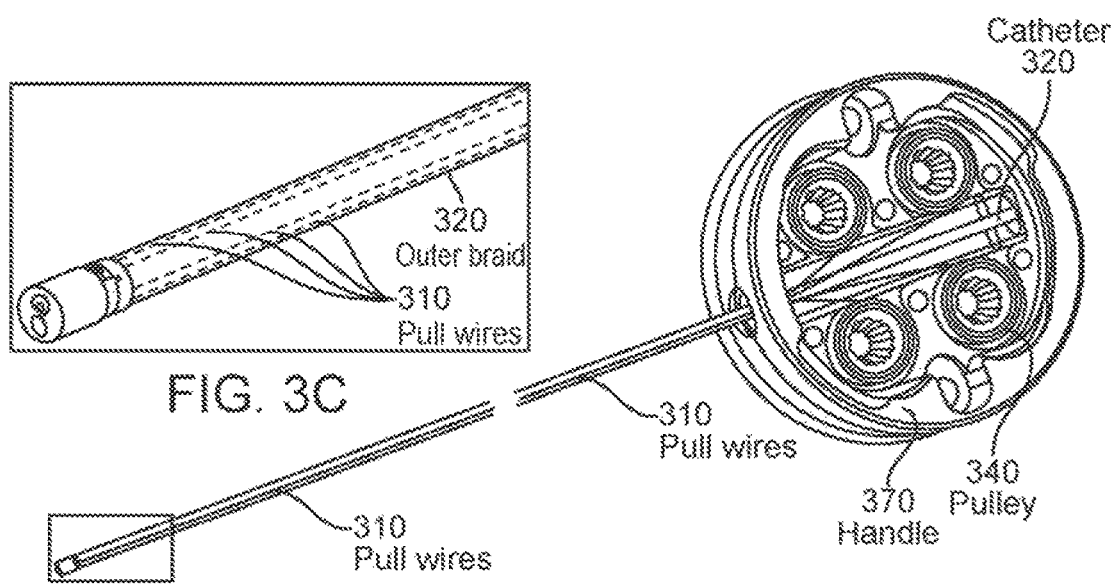
FIG. 3C
FIG. 3B

APPARATUSES AND METHODS FOR MONITORING TENDONS OF STEERABLE CATHETERS

CROSS REFERENCE TO RELATED APPLICATIONS

This application is a continuation of U.S. patent application Ser. No. 16/696,906, filed Nov. 26, 2019, which is a continuation of U.S. patent application Ser. No. 15/660,736, filed Jul. 26, 2017, which is a continuation of U.S. patent application Ser. No. 15/084,984, filed Mar. 30, 2016, which claims the benefit of U.S. Provisional Application No. 62/140,344, filed Mar. 30, 2015, which application is incorporated herein by reference.

The present invention relates to medical instruments, tools, and methods that may be incorporated into a robotic system, such as those disclosed in U.S. patent application Ser. No. 14/523,760, filed Oct. 24, 2014, U.S. Provisional Patent Application No. 62/019,816, filed Jul. 1, 2014, U.S. Provisional Patent Application No. 62/037,520, filed Aug. 14, 2014, U.S. Provisional Patent Application No. 62/057,936, filed Sep. 30, 2014, U.S. Provisional Patent Application No. 62/096,825, filed Dec. 24, 2014, and U.S. Provisional Patent Application No. 62/134,366, filed Mar. 17, 2015, the entire contents of which are incorporated herein by reference.

FIELD OF THE INVENTION

The apparatuses (including systems and devices) described herein may be related to steerable elongate devices. In particular, described herein are tendon-steerable elongate members suitable for medical applications in which tension and/or breakage of one or more tendons used to steer the device may be sensed.

BACKGROUND

Bending of elongate members such as steerable catheters allows these devices to be used in many beneficial ways, including when performing surgical procedures. For a catheter (and similar elongate, bendable members), articulation may be achieved by tensioning a tendon (also referred to herein as pull wire) which runs the length of the device, and is typically attached at the distal end, so that it can be actuated proximally. In a device with free floating tendons, wherein the tendons are not pre-tensioned, a certain level of slack within the catheter will likely exist. To remove the slack consistently, a tensioning algorithm based on measured force on the wire may be used. However, sensor size and placement can result in noise or inaccurate readings. Likewise, in the event of a wire breakage, external force sensors may detect a drop of tension on a wire, but may be unreliable, and may increase the complexity, size, and cost for the catheter.

One alternative to a traditional strain gauge is a resistance wire tension measuring gauge, such as described in U.S. Pat. No. 4,803,888, in which the electrical resistance of a wire was found to be related to the strain on the wire. To date, however, adapting such resistance measuring wires for us as part of a steerable guidewire has not been descried and/or successfully achieved. This may be due to the relative complexity of the tendon-drive elongate members, including the need for small diameters and the difficulty in accurately delivering power to the wire(s) acting as a strain gauge and the uncertainty associated with detecting a robust change in resistance with materials useful as tendons (wires) in steerable elongate members useful for medical applications.

Thus, it would be useful to provide tendon-steerable elongate devices such as catheters in which the tension on the tendon may be easily and accurately detected. Described herein are elongate, steerable devices, such as catheters, that are configured to directly measure the wire tension, as well as reliably detect wire breakage.

BRIEF SUMMARY

In general, described herein are tendon-steerable elongate apparatuses, and particularly medical apparatuses, that may be configured to easily and accurately detect strain on the tendons. Although the examples of tendon-steerable elongate devices provided herein are primarily elongate catheters for medical use, the features, principles and methods described herein may generally be adapted for use with any elongate tendon-steerable member, including steerable guidewires, sleeves, probes, or the like. Thus, the term "catheter" recited herein may refer to any type of elongate and tendon-steerable apparatus, including guidewires, sleeves, probes, etc.

Any of the apparatuses described herein may be a device and/or system (e.g., a related or interaction set of devices). For example, described herein are elongate catheter apparatuses having a plurality of tendons that are configured to be tensioned (e.g., pulled, and/or in some variations, pushed) to steer the apparatus, e.g., by bending the distal tip region (or an intermediate region) of the apparatus. The tendons may be electrically conductive (e.g., may comprise an electrically conductive material, such as steel and other alloys, including shape memory alloys (e.g., Nitinol). The apparatus may include, or may be configured to interact with, a sensing circuitry that can be put into electrical communication with the electrically conductive tendons of the apparatus, so that the sensing circuitry may detect, and in some cases respond to, tension on any of the tendons to which it is connected. The sensing circuitry may be on the elongate medical device (e.g., catheter), or it may be on a separate device that is placed in electrical contract/communication with the elongate medical device. For example, described herein are driving units, such as catheter steering units, that include sensing circuitry, to detect tension on one or more tendons (wires) of an elongate medical device when the driving unit/device is connected to a steerable elongate member such as a steerable catheter.

For example, described herein are steerable catheter systems that include: a plurality of electrically conductive tendons extending along a length of a steerable catheter; and a sensing circuit configured to be in electrical connection with the plurality of tendons, wherein the sensing circuit an electrical resistance of one or more tendon of the plurality of tendons.

Any of these steerable catheter systems may include: a steerable catheter, the steerable catheter comprising a body having an elongate length, a lumen extending through the elongate length, an electrically conductive outer member extending along the elongate length of the body, and a plurality of electrically conductive tendons each extending along the length of the catheter and having a proximal end region and a distal end region, wherein the distal end region of each tendon is coupled to a distal portion of the body so that applying tension a tendon of the plurality of tendons actuates bending of the catheter, wherein the plurality of tendons are electrically connected to the electrically conductive outer member at their distal end regions; and a sensing circuit configured to be in electrical connection with the plurality of tendons, wherein the sensing circuit detects an electrical resistance of one or more tendon of the plurality of tendons.

In some variations, the sensing circuit is configured to detect a change in the electrical resistance of the one or more tendons of the plurality of tendons. For example, the sensing circuit may be configured to identify a baseline electrical resistance for each tendon; this baseline may be used to automatically and/or manually adjust the tension of a tendon in the device.

The catheter may have any appropriate shape and/or additional features. For example, the catheter may comprise a body having an elongate length and one or more lumen extending through the elongate length. The catheter may include an electrically conductive outer member extending along the length of the steerable catheter.

The electrically conductive outer member may comprise a dedicated conductive (wire) for delivering voltage. In some variations the conductive outer member is all or a portion of the housing of the catheter, including a woven and/or braided outer layer of the braidwire. For example, in some variations, the catheter may include an electrically conductive outer braided member extending along the length of the steerable catheter in electrical contact with a distal end of the plurality of electrically conductive tendons. In some variations the conductive outer member is an electrically conductive tendon configured to deliver an electrical potential to a distal end of each tendon of the (other) plurality of tendons. In some variations, the electrically conductive outer member comprises an electrically conductive outer braid configured to deliver an electrical potential to a distal end of each tendon of the plurality of tendons.

As mentioned above, the tendons described herein may be used to actuate the elongate (e.g., catheter) member. A tendon may be a wire that is linear and/or coiled, flat, round, helical, or the like. The tendon is generally formed of a conductive material (in whole or in part) that changes resistance as it is placed under tension, and has a reasonable hysteresis property so that after the release of tension, the shape and electrical properties will return to pre-tensioned levels without undue delay (e.g., within 5 seconds, 2 seconds, 1 second, less than 1 second, 0.9 sec., 0.8 sec., 0.7 sec., 0.6 sec., 0.5 sec., 0.4 sec., 0.3 sec., 0.2 sec., 0.1 sec., etc.)

The tendons described herein may include a distal end region that may be mechanically coupled to a distal end region of the catheter so that applying tension to a tendon of the plurality of tendons bends the catheter. Further, the distal end regions of each of the tendons of the plurality of electrically conductive tendons may be electrically connected to each other, e.g., so that the same stimulation energy (e.g., applied voltage) may be applied across all of the tendons.

In general, a sensing circuit used with the tendon-articulating devices may be integrated into the tendon-driven, e.g., at a distal end region of the catheter. Alternatively or additionally, a sensing circuit may be included as part of a separate or separable driver. For example, the system may include a robotic driver unit configured to couple with the plurality of tendons and apply a proximal tension to the each of the tendons of the plurality of tendons; the sensing circuitry may be integrated into the robotic driver unit.

For example, described herein are robotic driver devices configured to couple with a plurality of tendons of a steerable catheter and apply a proximal tension to the each of the tendons of the plurality of tendons, the device comprising: a plurality of individually controllable drivers each configured to mechanically actuate a tendon of the plurality of tendons when the device is coupled with a catheter; a plurality of electrical contacts each configured to make an electrical connection with a tendon of the plurality of tendons when the device is coupled with a catheter; and a sensing circuit connected to the plurality of electrical contacts and configured to detect an electrical resistance of each of the one or more tendons of the plurality of tendons. These devices may include a voltage source configured to apply a bias voltage to an electrically conductive member of a catheter when the device is coupled with the catheter. These devices may include a plurality of sensing resistors of predetermined value, wherein each sensing resistor is in electrical communication with one of the plurality of electrical contacts and further wherein the sensing circuit is configured to measure the voltage drop across the sensing resistors to detect the electrical resistance of each of the one or more tendons of the plurality of tendons.

Any of the devices having a sensing circuit described herein may be configured to provide or evoke feedback when applying stimulation using the apparatus, e.g., to eliminate slack in the tendon. For example, a feedback circuit may be configured to control the tension applied to each of the plurality of individually controllable drivers based on the detected electrical resistance of each of the one or more tendons of the plurality of tendons when the device is coupled with a catheter.

Also described herein are steerable catheter devices configured to allow electrical detection of tension or breakage of a steering tendon. For example, a steerable catheter device may include: a body having an elongate length extending proximally to distally; at least one lumen extending through the elongate length; an electrically conductive member extending along the elongate length of the body; and a plurality of electrically conductive tendons each extending along the elongate length of the body and having a proximal end region and a distal end region, wherein the distal end region of each tendon is coupled to a distal portion of the elongate body so that applying tension to a tendon of the plurality of tendons actuates bending of the catheter; and wherein the distal end region of each tendon of the plurality of tendons is in electrical communication with the electrically conductive member.

In any of the apparatuses and methods described herein, the plurality of electrically conductive tendons may be electrically insulated.

In some variations, the steerable elongate device (e.g., catheter) may include a wire terminator at the distal portion of the body, wherein the distal end regions of each of the plurality of electrically conductive tendons terminates onto the wire terminator.

Methods of detecting the tension on and/or breakage of a tendon in an elongate and tendon-steerable medical device are also described herein. For example, described herein methods of detecting tension and breakage of a tendon in a steerable, elongate catheter. The method may include: applying an electrical potential along a tendon extending within the catheter; applying proximal tension to the tendon to steer the catheter; sensing an electrical resistance of the tendon; and determining a tension on the tendon or breakage of the tendon based on the electrical resistance of the tendon.

For example, described herein are methods of adjusting tension of a tendon in a steerable, elongate catheter, the method comprising: applying an electrical potential along a tendon extending within the catheter; sensing an electrical resistance of the tendon; and applying proximal tension to the tendon to steer the catheter based on the electrical resistance of the tendon.

In general, sensing an electrical resistance of the tendon may include measuring a voltage drop across a resistor having a predetermined value, wherein the resistor is electrically connected with the tendon.

The step of applying proximal tension may include applying tension based on the electrical resistance of the tendon.

Determining the tension on the tendon or breakage of the tendon based on the electrical resistance of the tendon may include determining the tension on the tendon or breakage of the tendon based on a change in the electrical resistance of the tendon.

The systems and apparatuses for detecting (via resistance of the tendon) tension on the wires/tendons used to steer these apparatuses may be configured to automatically, allow for manually, or both automatically and/or manually allow adjustment of the tendon based on the results of looking at tension (e.g., resistance) of the tendon. For example, the apparatus may be configured to regulate an amount of slack-reducing tension applied to the tendon based on the sensed electrical resistance of the tendon.

As mentioned, in general, any of these methods may include determining a tension on the tendon or breakage of the tendon based on the electrical resistance of the tendon.

A breakage may be detected by the apparatuses herein when, for example, the resistance of the tendon (or a group of tendons) rises steeply (e.g., appearing as an open circuit, with very, e.g., near infinite) resistance. If the sensing circuitry detects a breakage, it may trigger an alert when the sensed electrical resistance indicates that the tendon has broken.

Any of the methods described herein may include connecting the catheter to a robotic driver unit, wherein the robotic driver unit is configured to apply proximal tension to the tendon. For example, the methods may include connecting the catheter to a robotic driver unit, wherein the robotic driver unit is configured to sense the electrical resistance of the tendon.

In general, applying an electrical potential may include applying a voltage, and in particular, applying a voltage to a distal end of the tendon from an electrically conductive outer member extending along a length of the catheter.

Also described herein are methods of detecting tension and breakage of one or more tendon in a steerable, elongate catheter, the method comprising: applying an electrical potential along each of a plurality of tendons extending within the catheter; applying proximal tension to one or more of the tendons of the plurality of tendons to steer the catheter; sensing an electrical resistance of each of the tendons of the plurality of tendons; and determining a tension on at least one of the tendons of the plurality of tendons or breakage of at least one of the tendons of the plurality of tendons based on the electrical resistance of the at least one of the tendons of the plurality of tendons.

For example, described herein are methods of adjusting tension of a tendon in a steerable, elongate catheter, the method comprising: applying an electrical potential along a tendon extending within the catheter; sensing an electrical resistance of the tendon; and applying proximal tension to the tendon to steer the catheter based on the electrical resistance of the tendon.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A illustrates a schematic example of a catheter having a pair of tendons fixed at the distal end, in which the tendons are either not under tension or are under an equal amount of sleight tension (e.g., slack). FIG. 1B shows the apparatus of FIG. 1A with tension applied on the lower tendon to bend the distal end region down. FIG. 1C shows the apparatus of FIG. 1A in which a tendon has broken. In any of these examples, the resistance of the tendons may be used to detect tension and breakage.

FIGS. 2B and 2B1-2B2 are another example of a steerable catheter system configured to allow electrical detection of the resistance of a tendon to detect tension and breakage.

FIGS. 2C and 2C1-2C2 are another example of a steerable catheter system configured to allow electrical detection of the resistance of a tendon to detect tension and breakage, in which one of the tendons acts as the input voltage.

FIGS. 3A-3B illustrates a system including a catheter and robotic driver configured to allow electrical detection of the resistance of a tendon to detect tension and breakage. In FIG. 3A the catheter is shown being inserted into the robotic driver device, while FIG. 3B shows the catheter inserted into the robotic driver.

FIG. 3C shows the distal end region of the catheter of FIGS. 3A-3B.

DETAILED DESCRIPTION

Described herein are methods and apparatuses for detecting tension on a tendon (e.g., wire, pull wire, or cable). In particular, these apparatuses are steerable elongate apparatuses (generically, "flexible articulating devices") having one or more tendon that is electrically conductive and configured to bend (steer) the apparatus when tension is applied to the proximal end of the tendon. For example, described herein are methods and apparatuses for determining tension and/or breakage of one or more tendons by monitoring the electrical resistance of the tendon.

As used herein determining and/or measuring and/or monitoring tension of a tendon (also referred to herein as wires or pull wires) includes monitoring stress/strain on tendon. In particular, the apparatus may be configured to detect and reduce slack on the tendon by applying electrical energy through the tendon and detecting a corresponding resistance, where the resistance of the tendon is reflective of the mechanical load (tension, or stress/strain) on the tendon. For example, an apparatus as described herein may detect tension or monitor the stress/strain on the tendons (e.g., pull wires) by detecting the change in tendon resistance as tension is applied.

As will be described in greater detail below, this may include treating the tendon as a resistor of a circuit. When tension increases on the tendon, such as when the catheter is articulated or pushed against anatomy, the tendon stretches and thus increases in electrical resistance. To determine whether a tendon is broken or not, continuity in the circuit is examined. If the circuit is closed, in which a signal can pass through from the positive to negative terminal of the pull wire, then the tendon is intact. If the circuit is open, then a tendon has broken.

Figure 1A:
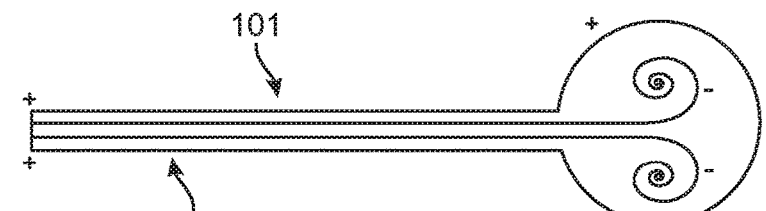
FIGS. 1A-1C schematically illustrates the operation of tendons (pull wires) to articulate a catheter and detect tension and/or breakage of the tendons.
Figure 1B:
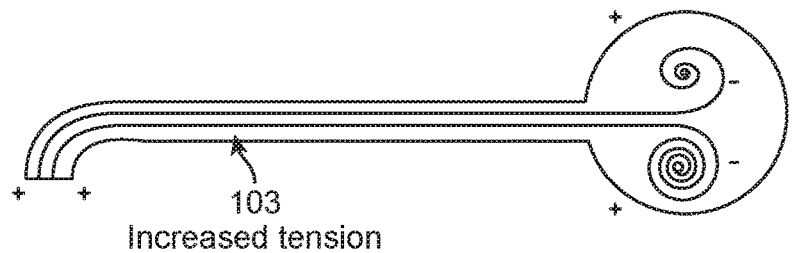
Figure 1C:
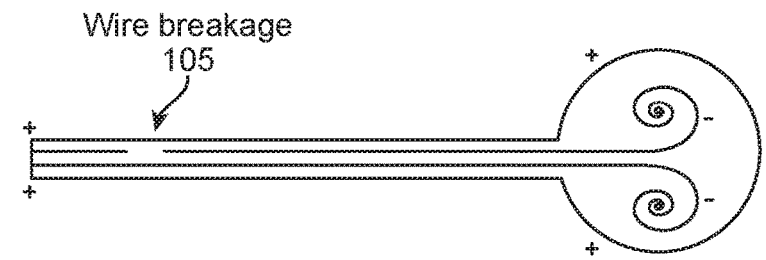

For example, FIGS. 1A-1C show illustrations of a schematic apparatus having a pair of tendons and further illustrates one example of a way to monitor the status of a catheter 101. In FIG. 1A, the two tendons are configured as variable resistors in a circuit which measures this resistance change; little if any tension is applied to the tendons, and the catheter is unbent. In FIG. 1B, one tendon 103 is articulated, there is an increase in tension, and thus a measurable increase in resistance through the articulated tendon. As shown in FIG. 1C, if a tendon breaks 105, the resulting "circuit" including the length of the tendon is an open circuit, e.g., so that the apparent resistance of the tendon approaches infinite.

Figure 2A:
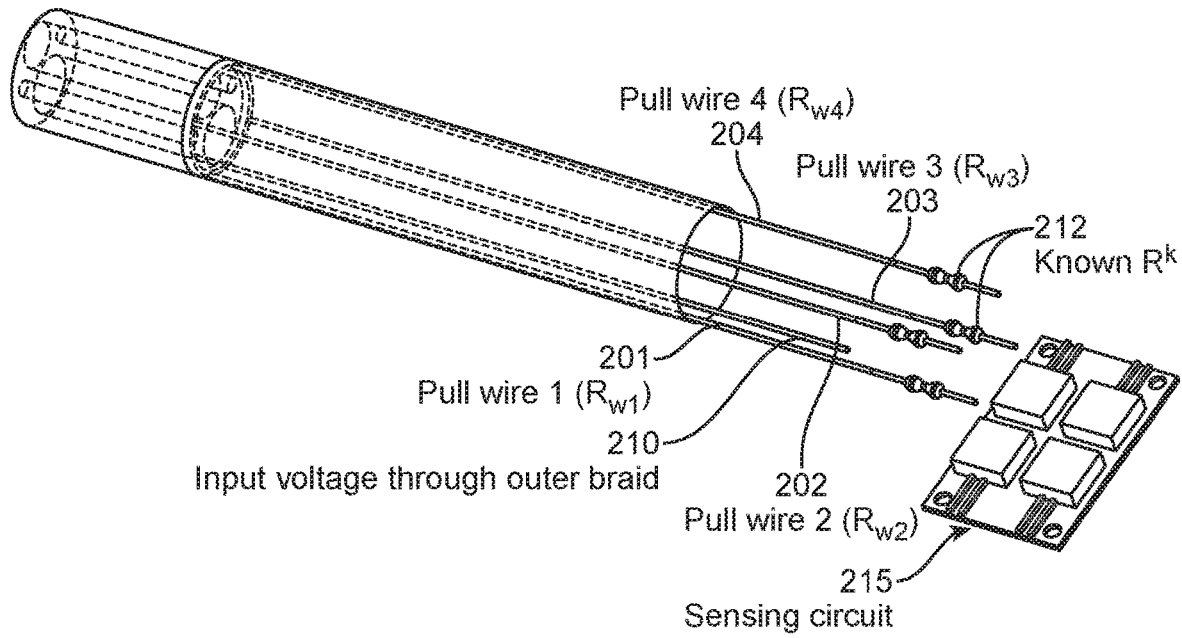
FIG. 2A shows one example of a catheter having electrically conductive tendons configured to allow electrical detection of tension and a sensing circuit.
Figure 4B:
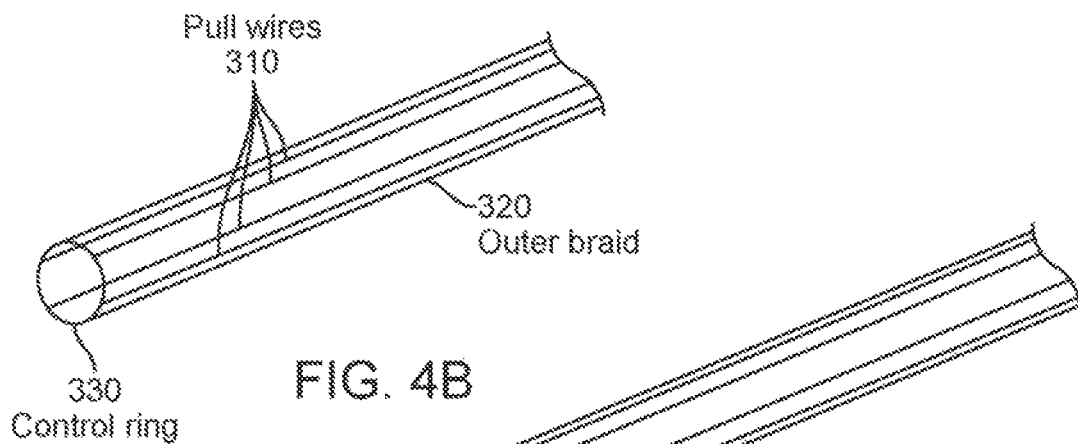
FIGS. 4A-4B illustrates an enlarged view of a distal end region of a catheter, similar to the variation shown in FIG. 3C.
Figure 4A:
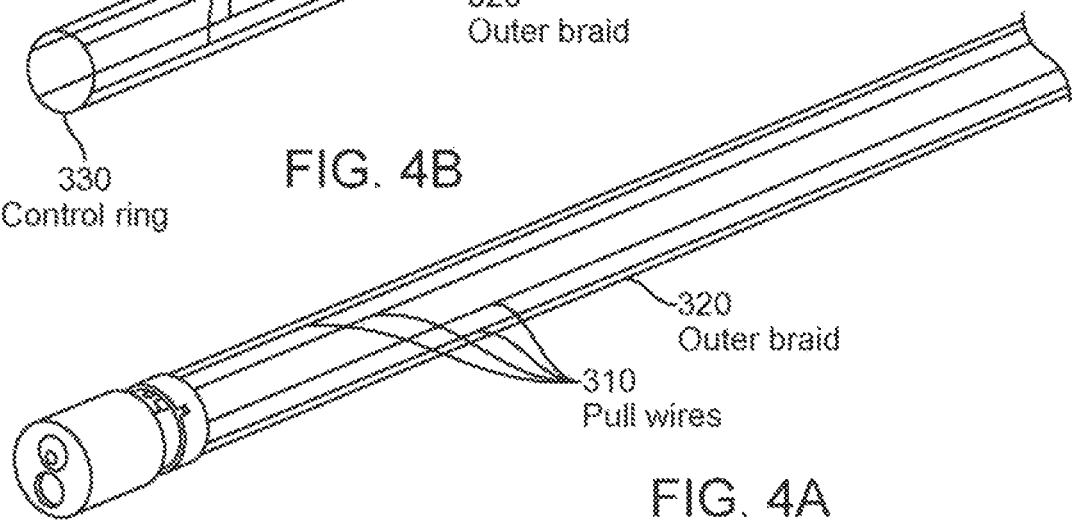

In general, the apparatuses described herein may include a metal tendon (pull wire), and a sensing circuit, as shown in FIG. 2A. In this example, the apparatus is a system including a catheter (a portion of which is shown in FIG. 2A, including the elongate body). In this example, four tendons 201, 202, 203, 204 extending within the lengths of the elongate body forming the catheter. Each tendon may be present in a channel within the elongate body. The catheter body (elongate body) may also include one or more lumen. Each pull wire may be treated as a variable resistor (e.g., Rw1, Rw2, Rw3, and Rw4) and may be separately or collectively monitored by the sensing circuit 215 after connecting to the sensing circuit (e.g., voltage measuring circuitry). In some variations, the connection/interface with the sensing circuit may include electrical contacts and known (fixed, predetermined value) resistors Rk across which the voltage drop may be measured. When an input voltage 210 is applied to the distal end regions of each of the tendons (pull wires), the resulting voltage drop detected may be used to determine the resistances of each of the tendons.

This is illustrated in different configurations in FIGS. 2B and 2C. For example, in FIG. 2B, the four tendons (pull wires 201, 202, 203, 204) are each mechanically and electrically connected at the distal end region to an electrically conductive wire terminator 206, and an input voltage is connected to the wire terminator. The input voltage may be delivered by any electrically conducive member; in FIG. 2B it is a wire extending proximally to the distal wire terminator. In some variations the input voltage (electrically conducive member or electrically conductive outer member) is a part of the body of the catheter, such as a braid of the braided outer sheath. The proximal ends of each tendon (pull wires 201, 202, 203, 204) are connected to resistors 221, 222, 223, 224 having a predetermined, known value. A sensing circuit 208 may be connected to each tendon 201, 202, 203, 204 through electrical wires 216; the sensing circuit 208 comprises voltmeters 211, 212, 213, 214 which measure the voltage (Vm) across each known resistor (Rk) 221, 222, 223, 224. From this configuration each of the resistances of the wires 201, 202, 203, 204 may be determined, as illustrated in the equations of FIG. 2B1, and an equivalent circuit is shown in FIG. 2B2.

Another example of a configuration that may be used to determine tension and/or breakage of a tendon is shown in FIG. 2C. In this example, one of the tendons (pull wire 201) is configured to operate as an input voltage (electrically conductive member), electrically connecting to each of the other tendons (pull wires, 202, 203, 204) at their distal ends. The proximal ends of the other tendons (pull wires 202, 203, 204) are connected to each other in parallel and connected to a known resistor 225 having a predetermined value, across which the voltage may be measured by the sensing circuitry to determine if a break has occurred in any of the tendons. An equivalent circuit for this is shown in FIG. 2C2, and relevant equations are shown in FIG. 2C1.

Any of the sensing circuits described herein may be configured to continuously or periodically monitor the resistance through one or more of the tendons 201, 202, 203, 204 when connected to the sensing circuitry. For example, any of the sensing circuits described herein may include a data acquisition card. The sensing circuit may be embedded and/or integrated into the catheter or into the driver, e.g., in the robot-side of the catheter/robot interface. The connection from the tendon to the system may be made through a tendon (pull wire) pulley and motor shaft, as illustrated in FIGS. 3A-3C and 4A-4B (showing a catheter system 300 comprising pull wires 310 enclosed within and coupled to an outer braid 320 through a control ring 320, the pull wires 310 being operatively coupled to a set of pulleys 340 and electrically connected to voltmeters 350 through an electrical connection 360 at handle end or instrument base 370) and 5A-5B (showing the pulleys 340 at the handle end or instrument base 370). Also, the positive (non-ground) terminal of the pull wires can be shared. The positive input is typically a constant voltage (DC). The opposite (e.g., negative) terminal can be used to measure resistance with an Ohmmeter or current.

Figures 5A, 5B:
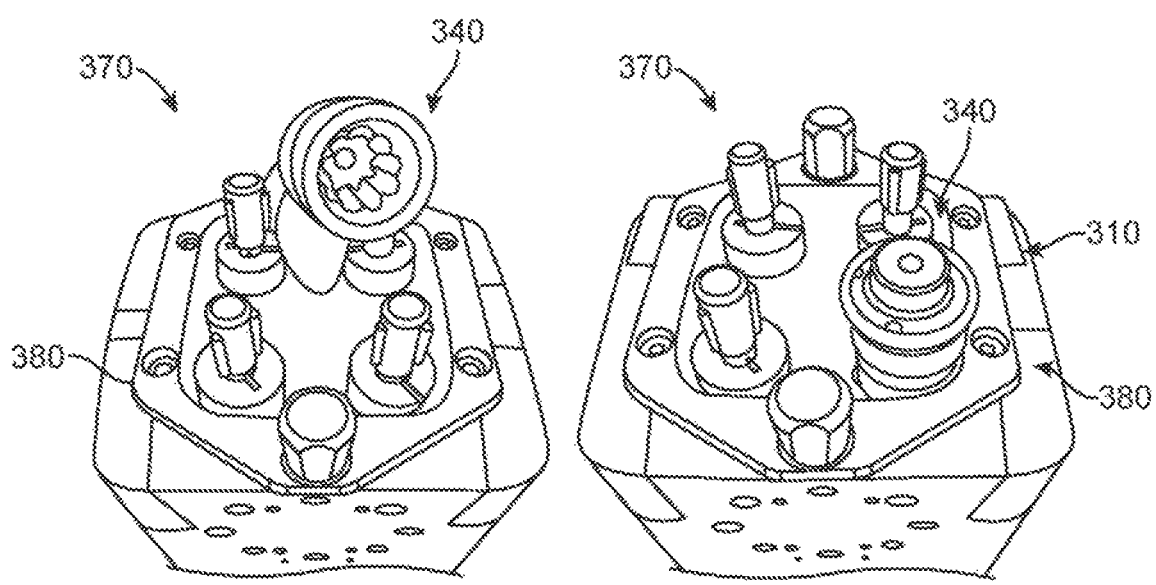
FIGS. 5A-5B illustrate example of a robotic drive device configured to allow electrical detection of the resistance of tendons of a catheter to detect tension and breakage of the tendon(s).

For example, FIGS. 5A and 5B illustrate a pull wire pulley 340 with a metal connector at the bottom, making electrical contact between the drive unit and the electrically conducive tendon. When the pulley 340 is placed onto the motor shaft of the drive unit 380, the electrical connection from catheter tendon (pull wire 310) to the sensing circuit 350 in the driver is made.

Figure 6A:
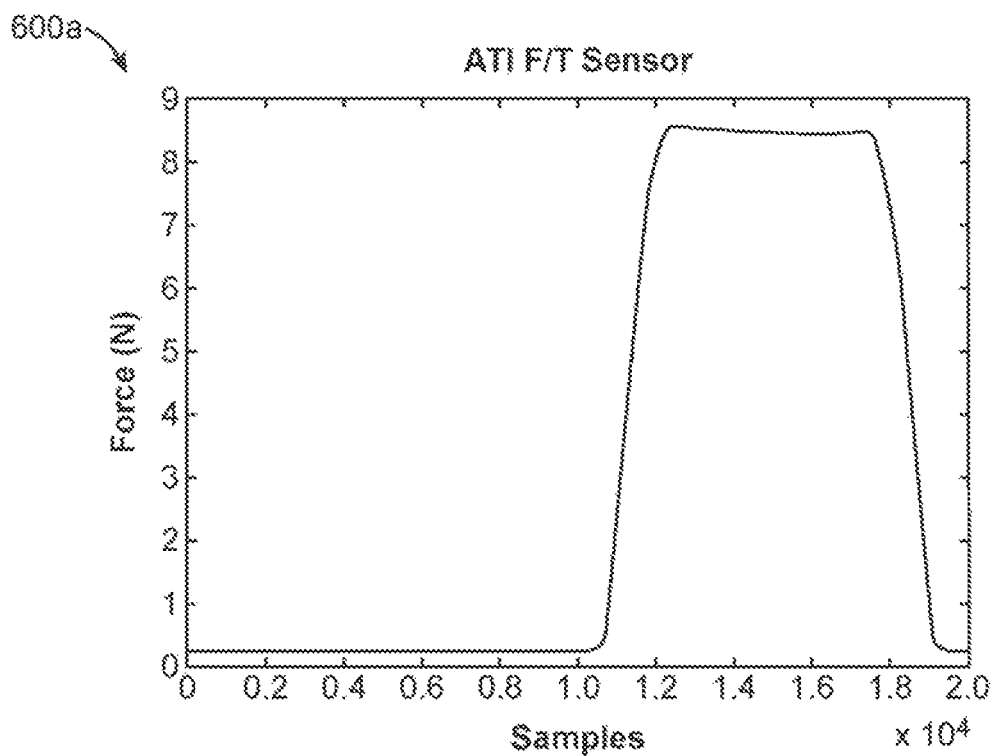
FIGS. 6A-6B illustrate one example of measurement of tension from a tendon wire showing the force applied to pull the tendon (FIG. 6A) and the detected resistance (FIG. 6B) of the tendon. The minimal force for the first half of the graph results from slack in the pull wire, resulting in a relatively constant (baseline) resistance for the tendon.
Figure 6B:
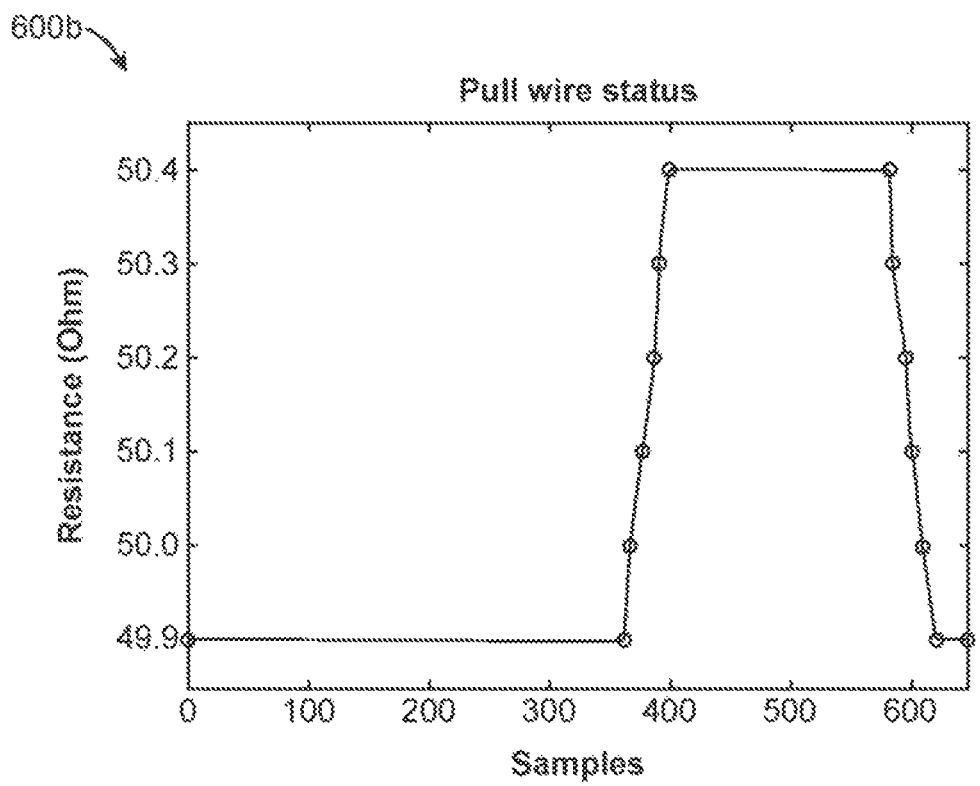
Figure 7A:
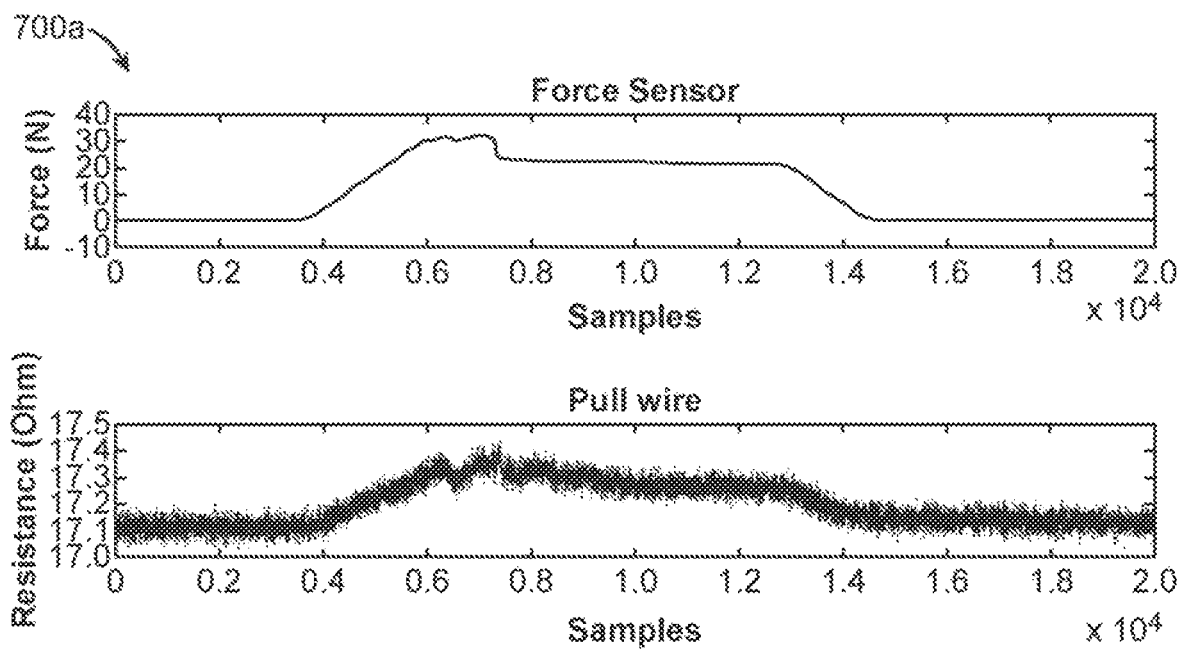
FIGS. 7A-7B show another example of tension being applied gradually to a tendon (FIG. 7A), and the resulting measured change in resistance (FIG. 7B).
Figure 7B:
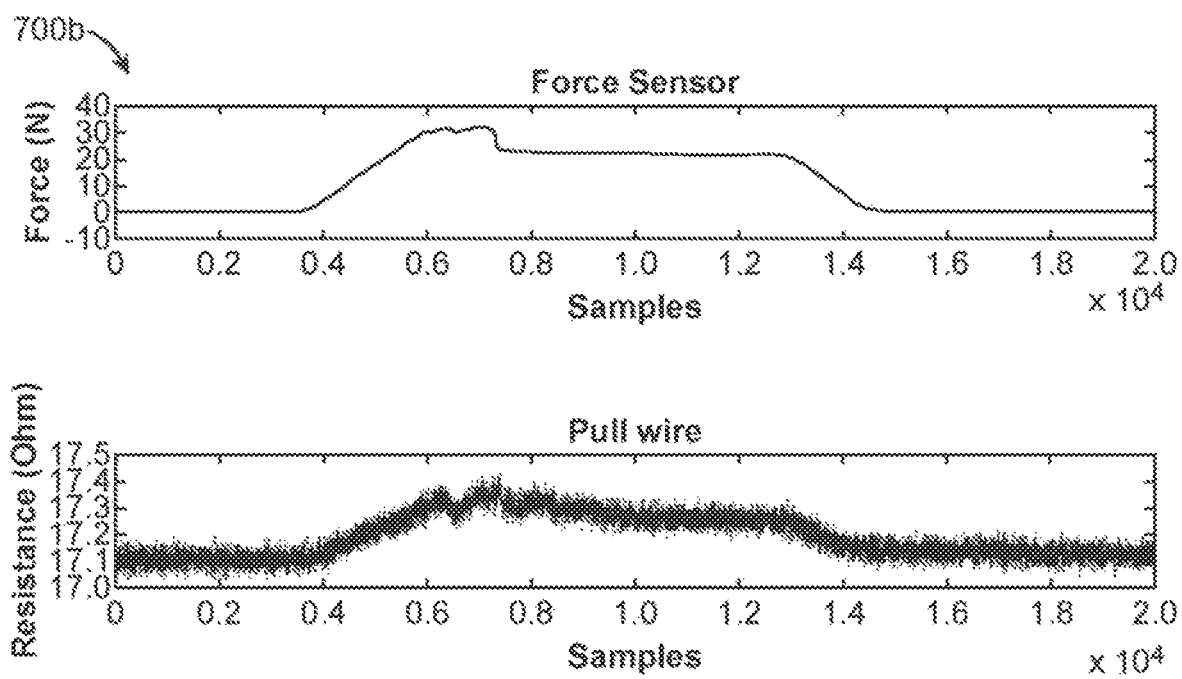
Figure 8A:
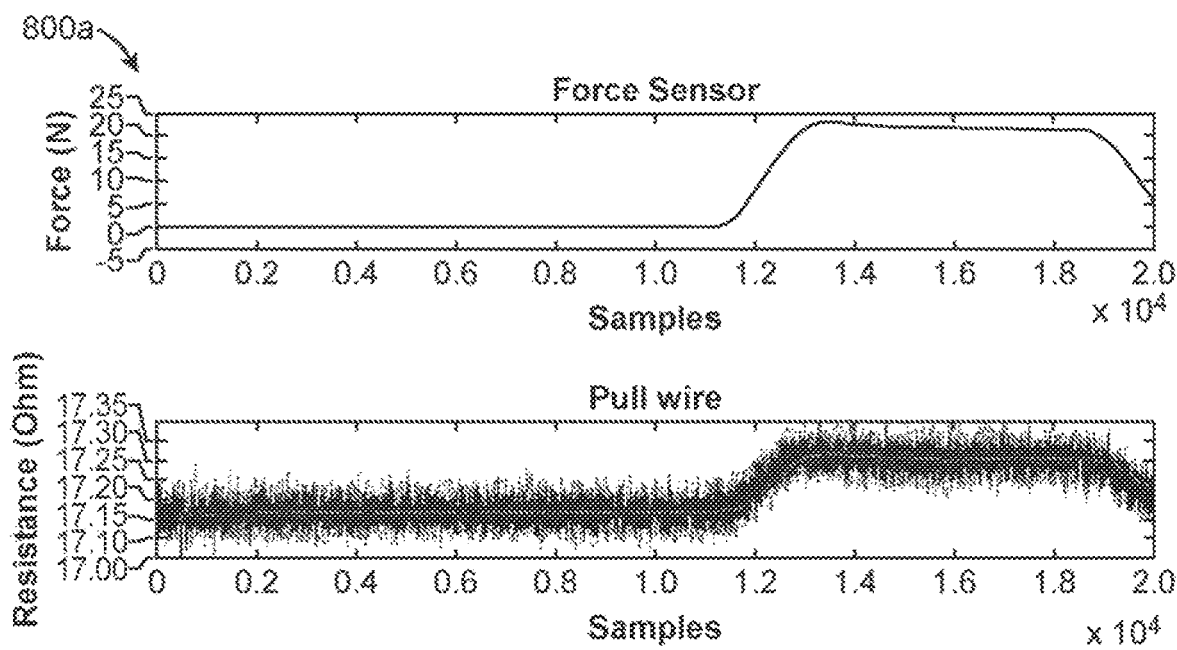
FIGS. 8A-8B show another example of tension being applied gradually to a tendon (FIG. 8A), and the resulting measured change in resistance (FIG. 8B).
Figure 8B:
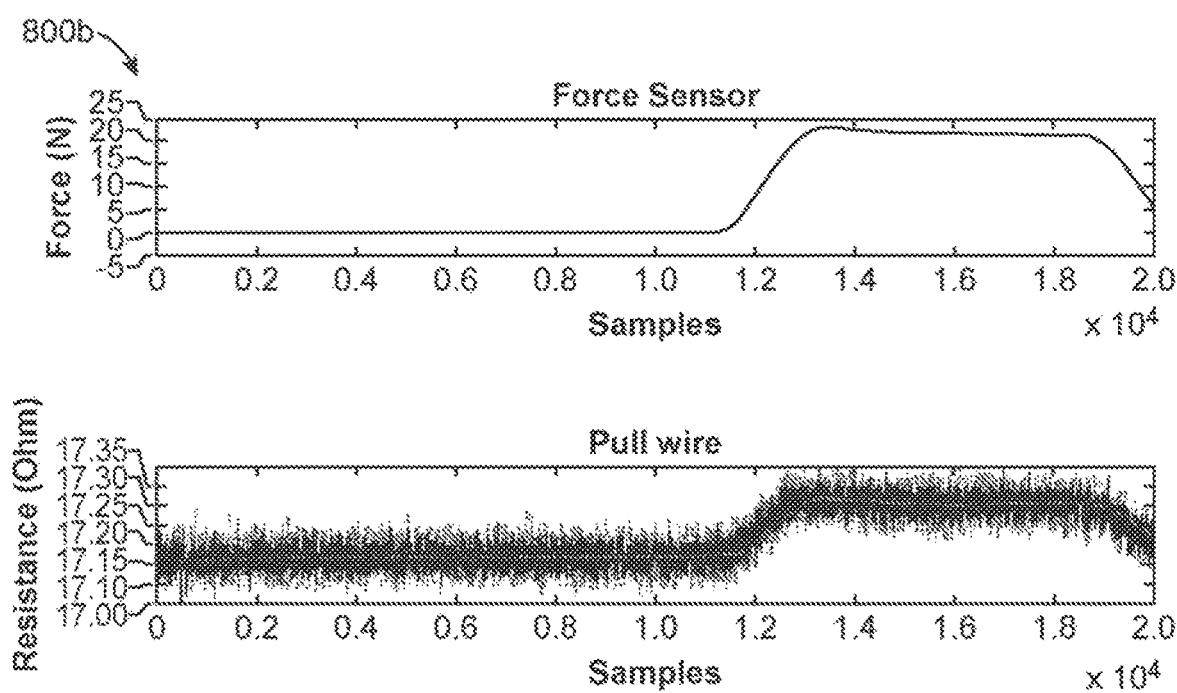

In one example, as shown in graphs 600a, 600b in FIGS. 6A-6B, a catheter tendon (e.g., 0.005" steel) was attached to an ATI force sensor on one end and a linear slide on another. The linear slide was moved to stretch the pull wire and the resulting tension was recorded on the ATI and the resistance change was recorded on the multimeter. 8.2 N of force corresponded to 0.5 Ohms of resistance. The applied force is shown in the graph 600a in FIG. 6A, while the resistance measured from the sensing circuitry is shown in the graph 600b in FIG. 6B. There is excellent agreement between the two, and the dynamic range of the resistance is between about 0.4-0.6 Ohms for this example. As seen, from about 3 mm of strain, the ATI force sensor measured 8.2 N of force, while the tendon resistance changed by approximately 0.5 Ohm. The change in resistance was approximately linear. The minimal force for the first half of the experiment is from slack in the pull wire. Thus the system was competent to detect when the first indication of force (when slack was eliminated) at approximately 1000 samples in.

FIGS. 7A-7B, 8A-8B and 9A-9B illustrate graphs 700a, 700b, 800a, 800b, 900a, and 900b, respectively, for other examples in which tensioning force was applied to a tendon, such as a tendon that may be used with a catheter as described herein, and the electrical resistance of the tendon reflected the tension and/or state (breakage, deformation, etc.) of the tendon. For example, in the graphs 700a in FIG. 7A, the force applied to a tendon was directly sensed by the change in resistance of the tendon, as seen in the graphs 700b FIG. 7B. Likewise, in the graphs 800a in FIG. 8A, up to 20 N of applied force (tension) was applied and detected by a change in the resistance of the tendon. In general, the sensing circuitry may include amplification and/or filtering of the signals (and detected resistances). For example, in the graphs 800b in FIG. 8B, the somewhat noisy resistance signal is shown both unfiltered and filtered (showing the smooth line within the raw signal).

Figure 9A:
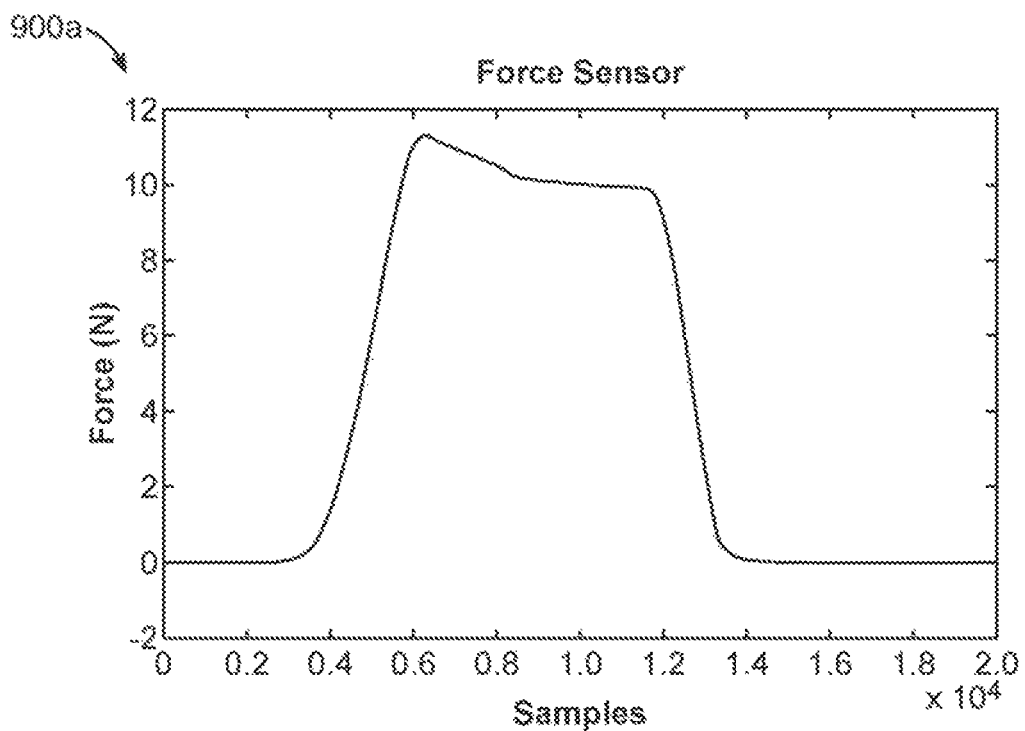
FIGS. 9A-9B show another example of tension being applied gradually to a tendon (FIG. 9A), and the resulting measured change in resistance (FIG. 9B).
Figure 9B:
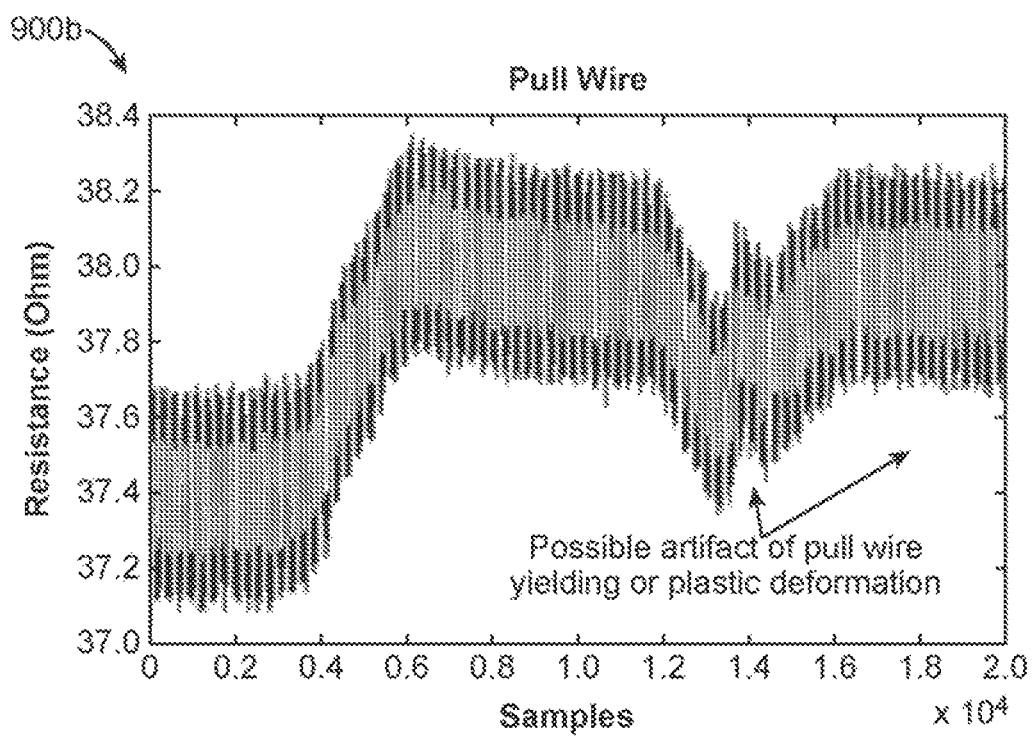

FIGS. 9A and 9B show graphs 900a and 900b, respectively, also illustrating the potential of this method to detect mechanical faults in the tendons, such as breakage and/or deformation. As illustrated in the graph 900b in FIG. 9B, when force was applied (shown in FIG. 9A), a deformation of the pull wire (yielding of the pull wire) resulted in a detectable shift of the baseline of the resistance value measured.

Using existing tendons (pull wires) in a catheter to monitor the health and performance of the device as described herein may be highly advantageous. For example, current state of the art tension sensing for catheters require expensive strain gauges, motor current estimation, or torque sensors. The methods and apparatuses described herein provide a cost-effective way of obtaining the same information. The methods and apparatuses also utilize existing catheter features, and only require a small modification to the catheter to system interface. In contrast, a piezoelectric strain gauge placed in-line with the pull wires would require additional wiring to the gauge.

In general, if a tendon underdoes excessive strain, it will exhibit permanent deformation. This may be detected by large changes in the resistance-to-tension calibration, and can be used as an indicator for compromised pull wire integrity, as illustrated above. In contrast, external sensors may only be able to estimate pull wire integrity. In addition, the methods and apparatuses described herein provide fast detection and computation, and do not require algorithms to filter data, while still allowing constant monitoring.

As mentioned above, in some variations, the sensing circuit may be within the apparatus (e.g., catheter). Such system may then pass a signal, including a digital signal, to the driver or other processor, indicating the tension and/or breakage (deformation, etc.) of the tendon.

As illustrated above in FIG. 2C, in some variations a simplified version of the method and/or apparatus may be used, in which tension sensing can be eliminated in favor of just wire breakage detection. Such detection circuits may be made even simpler and less expensively.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An articulatable instrument comprising:
    an elongated shaft;
    one or more electrically conductive pull wires that are elongated and run a length of the elongated shaft, the one or more electrically conductive pull wires being configured to be tensioned to cause mechanical articulation of the elongated shaft; and
    sensing circuitry configured to measure electrical resistance of the one or more pull wires.

2. The articulatable instrument of claim 1, further comprising an electrically conductive member extending along the length of the elongated shaft, the electrically conductive member being electrically coupled to the one or more electrically conductive pull wires.

3. The articulatable instrument of claim 2, wherein the electrically conductive member comprises a conductive wire.

4. The articulatable instrument of claim 2, wherein the electrically conductive member comprises a portion of an outer housing of the elongated shaft.

5. The articulatable instrument of claim 4, wherein the electrically conductive member comprises a braided sheath.

6. The articulatable instrument of claim 2, further comprising one or more resistors of the sensing circuitry, wherein each of the one or more resistors:
    is coupled in series with a respective one of the one or more pull wires; and
    has a known electrical resistance.

7. The articulatable instrument of claim 6, further comprising a conductive wire terminator disposed at a distal portion of the elongated shaft, wherein each of the one or more pull wires and the electrically conductive member is coupled to the wire terminator.

8. The articulatable instrument of claim 6, wherein:
    the sensing circuitry comprises one or more voltmeters, each of the one or more voltmeters being electrically coupled across a respective one of the one or more resistors; and
    the sensing circuitry is configured to measure electrical resistances of the one or more pull wires based at least in part on:
        a stimulation voltage applied to the one or more pull wires;
        an output voltage measured across each of the one or more resistors using one of the one or more voltmeters; and
        the known electrical resistance of the one or more resistors.

9. The articulatable instrument of claim 2, wherein a distal portion of each of the one or more pull wires is electrically coupled to a wire terminator associated with a distal portion of the elongated shaft.

10. The articulatable instrument of claim 9, wherein the one or more pull wires, the wire terminator, and the electrically conductive member are configured to allow for electrical current to pass in a circuit through the one or more pull wires, the wire terminator, and the electrically conductive member.

11. The articulatable instrument of claim 10, wherein the electrically conductive member is configured to receive an input voltage having an electrical potential that is different from a proximal portion of the one or more pull wires, thereby inducing an electrical current in the circuit.

12. The articulatable instrument of claim 2, wherein:
    the one or more pull wires comprises a plurality of pull wires enclosed within the elongated shaft; and
    the electrically conductive member comprises an outer sheath that is electrically isolated from the one or more pull wires along the length of the elongated shaft and electrically coupled to the one or more pull wires at a distal end of the one or more pull wires.

13. The articulatable instrument of claim 1, wherein a measured increase in the electrical resistance of at least one of the one or more pull wires indicates an increase in tension or breakage of the at least one of the one or more pull wires.

14. A method of monitoring an articulatable medical instrument, the method comprising:
    articulating a distal end portion of a medical instrument by tensioning an elongated pull wire that runs a length of an elongated shaft of the medical instrument;
    measuring an electrical resistance of the pull wire;
    determining a change in tension of the pull wire based on the measured electrical resistance; and
    in response to the change in tension of the pull wire, automatically tensioning the pull wire.

15. The method of claim 14, wherein said automatically tensioning the pull wire is performed using a robotic driver mechanically coupled to the medical instrument.

16. The method of claim 15, wherein said determining the change in tension is performed using sensing circuitry embodied in at least one of the medical instrument or the robotic driver.

17. The method of claim 14, wherein said measuring the electrical resistance of the pull wire is performed simultaneously with said articulating the distal end portion of the medical instrument by tensioning the pull wire.

18. The method of claim 14, wherein:
the pull wire is electrically coupled to a wire terminator at a distal area of the elongate shaft;
the wire terminator is electrically coupled to an electrically conductive member; and
sensing circuitry is electrically coupled to the pull wire and the electrically conductive member to form a circuit.

19. The method of claim 18, wherein at least one resistor is coupled to the pull wire as part of the circuit, the at least one resistor having a known electrical resistance, the sensing circuitry being configured to read a voltage across the at least one resistor.

20. The method of claim 19, wherein said measuring the electrical resistance involves generating an electrical current through the circuit and determining a voltage drop across at least one of the pull wire or the at least one resistor.

\* \* \* \* \*